United States Patent
Nagayama et al.

[11] Patent Number: 5,610,392
[45] Date of Patent: Mar. 11, 1997

[54] METHOD TO OBSERVE FILM THICKNESS AND/OR REFRACTIVE INDEX BY COLOR DIFFERENCE

[75] Inventors: Kuniaki Nagayama, Tokyo; Eiki Adachi, Ibaraki, both of Japan

[73] Assignee: Research Development Corporation of Japan, Saitama, Japan

[21] Appl. No.: 537,117

[22] Filed: Sep. 29, 1995

Related U.S. Application Data

[63] Continuation of Ser. No. 231,120, Apr. 22, 1994, abandoned.

[30] Foreign Application Priority Data

Apr. 23, 1993 [JP] Japan .................................. 5-097794
Jun. 23, 1993 [JP] Japan .................................. 5-152247

[51] Int. Cl.$^6$ .......................... G01N 21/21; G01B 11/06; G01J 3/50
[52] U.S. Cl. .................. 250/226; 250/225; 250/559.23; 250/559.27; 356/381; 356/369
[58] Field of Search ................................ 250/559, 560, 250/571, 574, 573, 225, 226, 559.01, 559.23, 559.27; 356/381, 369, 445, 355

[56] References Cited

U.S. PATENT DOCUMENTS

| | | | |
|---|---|---|---|
| 4,207,467 | 6/1980 | Doyle | 250/338 |
| 4,606,641 | 8/1986 | Yamada et al. | 256/369 |
| 4,695,162 | 9/1987 | Itonaga et al. | 356/369 |
| 5,018,863 | 5/1991 | Vareille et al. | 356/369 |
| 5,107,105 | 4/1992 | Isobe | 250/225 |
| 5,329,357 | 7/1994 | Bernoux et al. | 356/369 |
| 5,333,052 | 7/1994 | Finarov | 356/369 |

OTHER PUBLICATIONS

"Differential Ellipsometry", T. Sandströ, Journal de Physique, Colloque C10, supplement au No. 12 Tome 44, Dec. 1983, pp. C10-75-C10-78.

"The Use of The Isocope Ellipsometer In The Study of Adsorbed Proteins And Biospecific Binding Reactions", M. Stenberg and H. Nygren, Journal de Physique, Colloque C10, supplement au No. 12 Tome 44, Dec. 1983, pp. C10-83-C10-86.

"Spatially Resolved Ellipsometry", M. Erman and J. B. Theeten, J. Appl. Phys., vol. 60, No. 3, 1 Aug. 1986, pp. 859-873.

"Performance Of A Microscopic Imaging Ellipsometer", D. Beaglehole, Rev. Sci. Instrum 50 (12), Dec. 1986, pp. 2557-2559.

"Ellipsometric Microscopy. Imaging Monomolecular Surfactant Layers At The Air-Water Interface", R. Reiter et al., Langmuir, vol. 8, No. 7, 1992, pp. 1784-1788.

*Primary Examiner*—Stephone Allen
*Attorney, Agent, or Firm*—Wenderoth, Lind & Ponack

[57] ABSTRACT

To observe film thickness and/or refractive index of a sample, light beams from a white light source are irradiated onto the surface of the solid or liquid sample such that the reflected light beams are colored by partial extinction of the reflected light beams. A difference 17 film thickness and/or refractive index of the sample is observed according to color difference of the reflected light beams.

7 Claims, 3 Drawing Sheets

METHOD TO OBSERVE FILM THICKNESS AND/OR REFRACTIVE INDEX BY COLOR DIFFERENCE

This application is a Continuation of now abandoned application, Ser. No. 08/231,120, filed Apr. 22, 1994.

FIELD OF THE INVENTION

The present invention relates to a method for observing film thickness and/or refractive index according to a color difference. More particularly, the present invention relates to a method for observing film thickness and/or refractive index according to a color difference which is useful for the development and evaluation of new materials.

PRIOR ART

The study of a surface condition is very important in the development and evaluation of new materials, and in the electronics industry. In the production of a silicon oxide film on a silicon wafer board, for example, two-dimensional film thickness distribution for the silicon oxide film must be confirmed by surface analysis with nanometer-order precision.

It is thus necessary to observe film thickness, and further, refractive index, of a solid or a liquid as a two-dimensional distribution or a dynamic change.

Conventional surface analysis methods, most of which derive from a scanning microscope, include Auger, ESCA, and EPMA, which are useful for local presence of materials, and materials analysis.

Secondary ion-mass spectrography (SIMS), one of the conventional methods, is used to measure materials distribution in the depth direction.

However, only the optical methods provide a means to evaluate film thickness and optical properties at a high precision, whatever the materials may be.

An optical method includes a technique to measure the intensity of transmitted and fluorescent light, but an ellipsometer is the most reliable in the measurement of film thickness.

Several types of ellipsometers have been developed in recent years to allow dynamic measurement of the two-dimensional distribution of film thickness and/or refractive index of a thin film on the surface of a material. These ellipsometers are used very often in various methods today. The ellipsometric method may be classified into two types as follows:

(1) A first method which measures two-dimensional distribution by measuring film thickness and refractive index of a sample using a light beam which is squeezed into a spot in the order of 10 μm in diameter while moving the sample over a plane (M. Erman and J. B. Theeten, J. Appl. Phys., 60, 859 [1986]).

(2) A second method which records multiple images of the intensity of reflected light beams on a detector using a CCD camera to calculate two-dimensional distribution of film thickness and refractive index of a thin film placed on a substrate (D. Beaglehole, Rev. Sci. Instrum., 59, 2557 [1988]).

The former method (1) inevitably involves mechanical vibration because the sample must be moved in the measurement. In addition, the method is not applied to the measurement of liquid surfaces. Further, it takes much time to scan a sample because the motion of the sample is mechanical.

The latter method (2) requires acquisition of multiple digitized images of the intensity of reflected light beams. This involves much time for completing a run. Further, dozens of images are necessary to derive a practical level of precision in the measurement of refractive index, and this in turn necessitates the use of a huge memory capacity or an external memory. Similar complex measuring steps must be followed, and thus similar time usage is necessary, for deriving the two-dimensional distribution for just a single refractive index.

The present invention was developed in consideration of the above circumstances and intends to solve the problems in the conventional methods by providing a novel method for observing film thickness and/or refractive index; confirming two-dimensional distribution of refractive index and film thickness and their dynamic change with ease and visually; observing surface phenomena on a real time basis, and measuring a liquid surface.

SUMMARY OF THE INVENTION

To solve the above problems, the present invention provides a method to observe film thickness and/or refractive index according to color difference wherein light beams from a white light source are irradiated on to the surface of a solid or liquid and the reflected light beams are colored by partial extinction of the reflected light beams to observe the difference of film thickness and/or refractive index according to color difference.

The present invention further provides a method to observe film thickness and/or refractive index at an enhanced sensitivity with an increased color difference wherein the reflected light beams are incident on the surface of the same solid or liquid again, repeating this re-incidence more than once, and the reflected light beams are colored by partial extinction of the reflected light beams to observe the difference of film thickness and/or refractive index with an increased color difference.

DETAILED DESCRIPTION OF THE INVENTION

Figure 1:
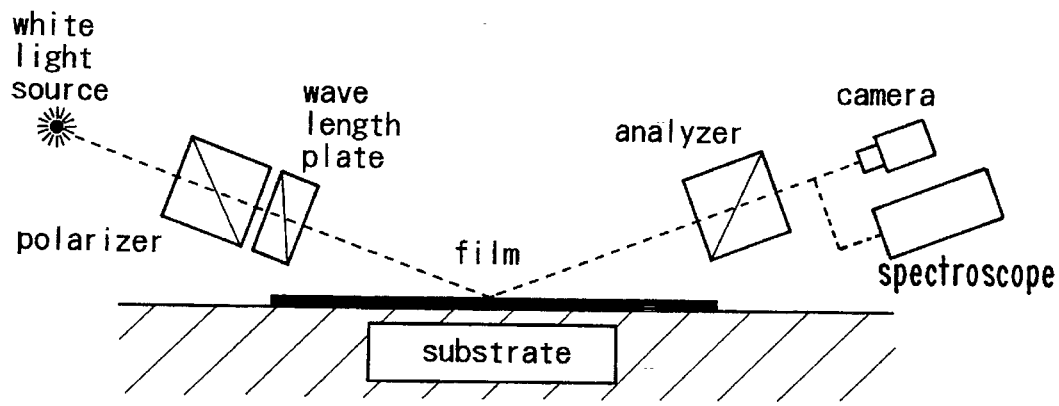
FIG. 1 is a structural view illustrating an example of a system for partial extinction of reflected light beams according to the method of the present invention.

The basic feature of the present invention consists of the partial extinction and the coloring of reflected light beams as described above. This feature permits observation of the difference in film thickness and/or refractive index according to color difference.

The above feature permits:

[1] Observation of film thickness and/or refractive index distribution according to the difference in color.

[2] Real-time observation of surface phenomena. [3] Possibility of observation of a liquid surface because the sample may not be moved in the measurement.

Further, all of these observations can be performed at a high sensitivity.

The working of the present invention is described first with respect to the extinction method (principle of the extinction type ellipsometer) followed by a description of partial extinction.

Extinction Method

The extinction method is described below. The condition of a polarized light beam is defined by the following formula:

$$\rho = \tan \psi \cdot e^{i\Delta} = \frac{E_p}{E_s} \quad (1)$$

where Ep and Es are p and s components of the electric field vector of a light beam, respectively. Is a ratio of the electric field vector, "$\Delta$" is a phase difference therebetween, and "i" is the square root of negative 1. Next, we consider the surface of a substrate covered with a film. For incident monochromatic light, with an oblique angle polarization of the reflected light beams is expressed by $$\rho = \frac{E_p}{E_s} = \frac{R_p}{R_s} \cdot \frac{E_p^o}{E_s^o} \quad (2)$$

By using the following relations $$\frac{R_p}{R_s} = \tan \psi_s \cdot e^{i\Delta_s} \quad (3)$$

$$\frac{E_p^o}{E_s^o} = \tan \psi_o \cdot e^{i\Delta_o}$$

we obtain:

$$\rho = \tan \Psi_s \cdot \tan \Psi_o \cdot e^{i(\Delta_s + \Delta_o)} \quad (4)$$

where Rp and Rs are complex reflectivity of the relevant surface. Film thickness, refractive index of the film, refractive index of the substrate, and the incident angle of light beams are dependent on wavelength. By assuming that refractive index of the substrate, incident angle of light beams, and wavelength are known. Ep and Es are p and s components, respectively, of the electric field vector of the incident light beam. Assuming these are known as well, then we can treat the light as linear polarization when the following equation is satisfied:

$$\Delta_s + \Delta_0 = m\pi (m \text{ is integral number}) \quad (5)$$

Equation (5) indicates that the reflected light beams can be changed into linearly polarized light beams at any time simply by adjusting $\Delta_0$. Linearly polarized light beams can be extinguished by a polarizer. Based on the direction of the electric field vector in this instance, $\Psi$ to satisfy $\tan \Psi = \tan \Psi_s \cdot \tan \Psi_0$ can be known. Since $\Delta_0$ and $\Psi_0$ are known, $\Delta_s$ and $\Psi_s$ can be known readily. Since film thickness and refractive index of film are the only two unknowns, these can be known from $\Delta_s$ and $\Psi_s$. This is the principle of the extinction method in the ellipsometer.

Partial Extinction.

Partial extinction is described below.

Assume the light source is a white light. A white light contains all light wavelengths at the same intensity. In this instance, generally, $\Delta_s$ and $\Psi_s$ are a function of wavelength. When equation (5) is satisfied for a given wavelength in a given incident light with respect to said wavelength, incident angle, film thickness, refractive index for said wavelength, and refractive index of the substrate for said wavelength, then, generally, equation (5) is not satisfied for any other wavelength, and the reflected light beams are linearly polarized only at said single wavelength. Accordingly, only one wavelength can be extinguished when using a polarizer. This is called partial extinction. The partially extinct light beams are colored in the complementary color for the extinct color.

FIG. 1 shows an example of a system for partial extinction. The substrate surface to be observed is covered with a thin film of a certain refractive index distribution. A white light source is generally used for an ordinary extinction type ellipsometer. Reflected light beams pass through a detector (that is, polarizer). By properly adjusting the angle of the detector and the polarizer on the incident side, partial extinction takes place on the surface of the substrate at a certain wavelength corresponding to the given thin film thickness and refractive index. The first axis (optical high speed axis) of the wave plate is set in the 45 or 135-degree direction.

Figure 3:
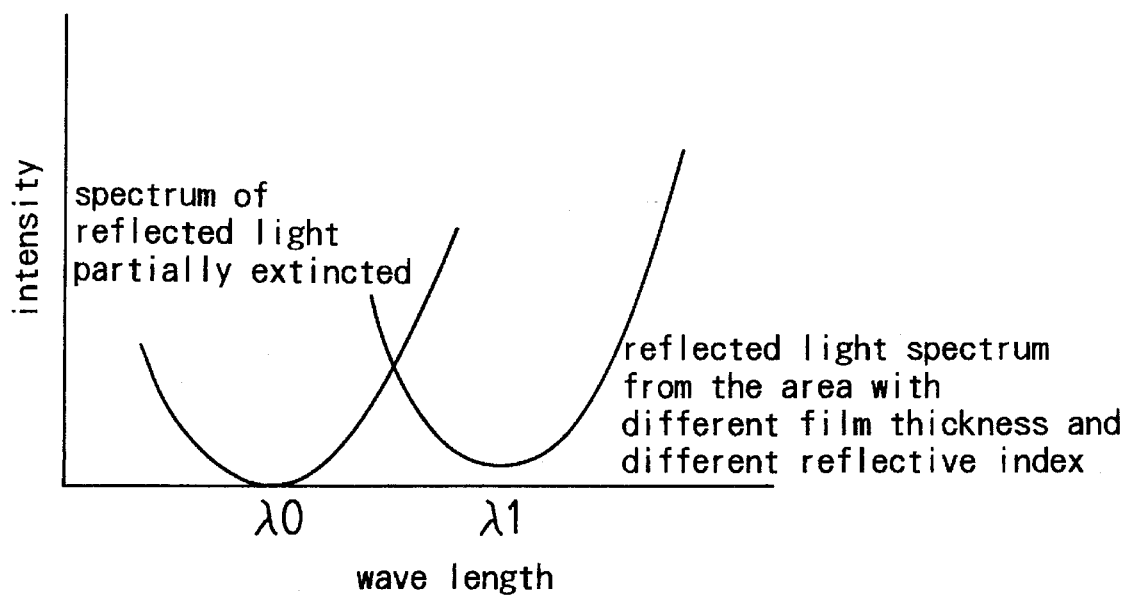
FIG. 3 is a diagram illustrating the relation between the spectral intensity of reflected light beams partially extinguished and spectral intensity of reflected light beams from the area having a different film thickness and refractive index.

The reflected light beams in this instance are tinted certain color corresponding to a specific film thickness and refractive index because the light beams are partially extinct. The area whose refractive index is the same as the above is the place where similar partial extinction takes place, and is tinted in the same color. Spectral intensity of the reflected light beams in this instance reaches the lowest level at the wavelength ($\lambda 0$) where partial extinction took place, as shown in FIG. 3 for example. All other locations have a different refractive index, so that the light beams reflected from there are not linearly polarized at any wavelength, and thus are not partially extinct. The spectral intensity reaches the lowest level at a different wavelength ($\lambda 1$). When the smallest wavelength is different, the color is also different, with the result that one will see different colors depending on location. It is possible to shoot the reflected light beams with a camera.

Enhanced Sensitivity

The $\Delta_s$ in equation (5) doubles when the light beams from the surface of the sample in the above method is reflected from a mirror and re-incident on the same surface. This means that the light beams reflected from the same surface twice are polarized two times larger than those reflected only once. The difference in polarization of other reflected light beams from other locations on the same sample having a different film thickness and/or refractive index also doubles. As a result, the color difference increases. This suggests that a very small difference in film thickness and/or refractive index may possibly be identified according to a color difference.

Figure 2:
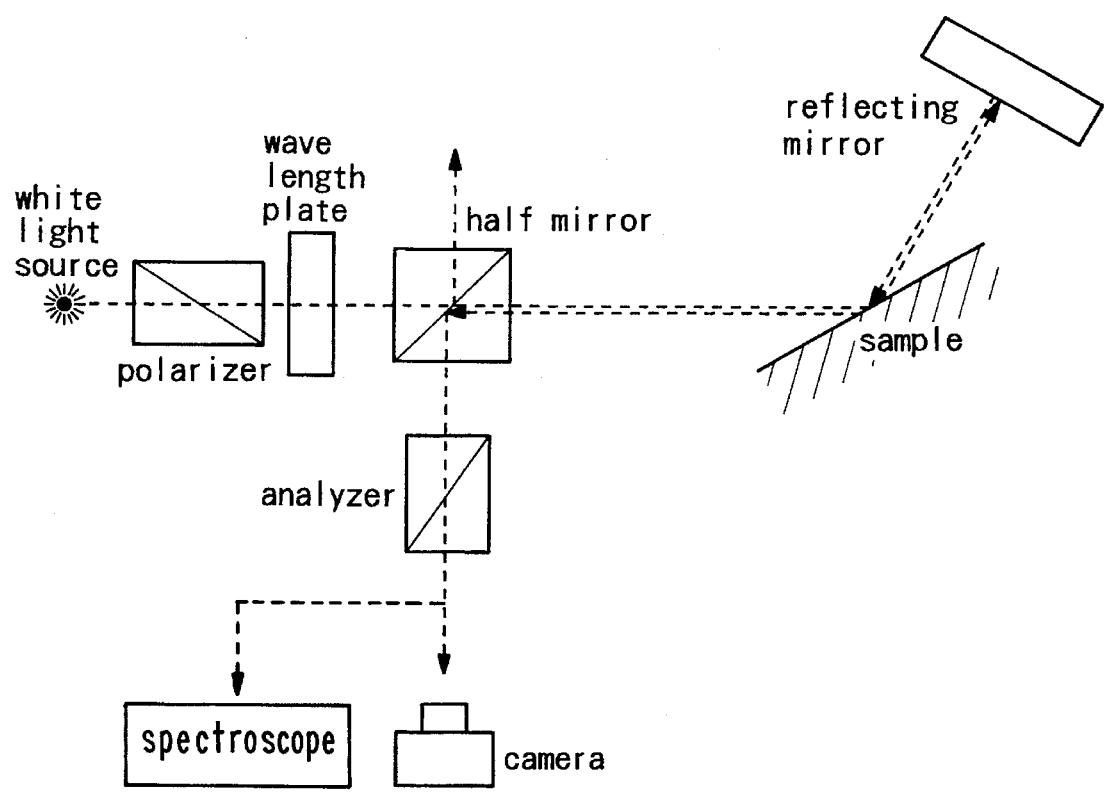
FIG. 2 is a structural view illustrating an example of a system for partial extinction of reflected re-incident light beams according to the method of the present invention.

When the reflected light beams are re-incident on the same surface more than twice, then more sensitive observation is possible. Of course, attenuation of the reflected light beams must be considered. FIG. 2 shows an example of a system by which the reflected light beams are repeatedly incident on the same surface.

It goes without saying that various embodiments are possible for the present invention which is based on the above working principle. For example, in the present invention, the detecting device may be a spectroscope, in which case quantification is possible. A camera, color CCD camera, spectroscope and other devices may also be used. When specific correspondence between color and film thickness is predetermined for a specific sample, then one can determine film thickness by observing color with a camera or a color CCD camera. In this case, of course, identification is impossible unless the color difference due to different film thickness has at least a certain size. When this condition is satisfied, film thickness can be accurately determined by the color observed under the spectroscope.

Working examples are shown below to further describe the present invention in detail.

Working Example 1

The FIGS. 1 and 2 show examples of a system for the present invention. In the present invention, as shown in FIG. 1, light beams from a white light source are specifically polarized by a polarizer and a wave plate and are incident on the surface of a sample. The condition of polarization varies and the light beams are reflected from the sample surface, and pass through a detector, finally reaching a camera. The system shown in FIG. 2 allows observation at an enhanced sensitivity. Light beams are incident on and reflected from the surface of a sample, are further reflected from a reflector, and incident on the surface of the same sample again. The condition of polarization also varies here. The light beams are reflected from a half mirror at 90 degrees, and pass through a detector, finally reaching a camera.

It is important, in this instance, to keep in mind that the reflectivity of the half mirror depends on polarization. The dependency should be as small as possible. The reflectivity of the half mirror to be used should not depend on wavelength excessively.

Working Example 2

The difference of film thickness was actually observed on the surface of a silicon wafer substrate using the system shown in FIG. 2: which is constructed in Working Example 1.

The sample was a silicon wafer provided with an oxide film which was about 2 nm thick. A resist film was applied to the surface of the sample. The sample was immersed in a 10% HF solution for about 30 seconds, and then washed in pure water, and the resist film was removed with acetone, ready for observation. The area protected by the resist film was covered with the oxide film which retained its original thickness. The resultant surface had a profile in the depth direction.

A halogen lamp was used as the light source. Prisms were used as the polarizer and detector. The angle of the polarizer and detector was so adjusted as to extinguish 550 nm wavelength using the system shown in FIG. 2. The result was shot with a camera.

The area of residual oxide film was white and the surrounding area was blue. The $\Delta$ of the oxide film was 168 degrees and $\Psi$ was 11.8 degrees. Those for the surrounding area were 172 and 11.8 degrees, respectively. These differences are equivalent to approximately 1 nm as the difference of film thickness.

As described above in detail, the present invention makes it possible to discern film thickness and refractive index distribution according to color difference and observe surface phenomena on a real-time basis. It further enables more sensitive observation. Liquid surfaces can also be observed because it is not necessary to move samples in the observation.

What is claimed is:

1. A method for observing a distribution of at least one of a film thickness and a refractive index along a two-dimensional surface area of an object, the object being one of a solid and a liquid, said method comprising:

irradiating light beams of multiple wavelengths from a white light source onto the two-dimensional surface area of the object to obtain a reflected two-dimensional color image of the two-dimensional surface area of the object such that resultant reflected light beams of multiple wavelengths forming the reflected image of the two-dimensional surface area of the object are colored by partial extinction of a single wavelength of the light beams of multiple wavelengths from the white light source; and, observing a distribution of at least one of a film thickness and a refractive index along the two-dimensional surface area of the object according to a color distribution of the reflected two-dimensional color image of the two-dimensional surface area of the object.

2. A method as claimed in claim 1, wherein a polarizer is interposed between the white light source and the object to achieve the partial extinction of the single wavelength of the light beams of multiple wavelengths from the white light source.

3. A method as claimed in claim 2, wherein a spectroscope is used for quantitative detection of the reflected light beams of the reflected two-dimensional color image of the two-dimensional surface.

4. A method as claimed in claim 1, wherein a spectroscope is used for quantitative detection of the reflected light beams of the reflected two-dimensional color image of the two-dimensional surface.

5. A method for observing a distribution of at least one of a film thickness and a refractive index along a two-dimensional surface area of an object, the object being one of a solid and a liquid, said method comprising:

irradiating light beams of multiple wavelengths from a white light source toward the two-dimensional surface area of the object and redirecting resultant reflected light beams of multiple wavelengths back to the two-dimensional surface area of the object at least once to obtain a reflected two-dimensional color image of the two-dimensional surface area of the object such that resultant further reflected light beams of multiple wavelengths forming the reflected image of the two-dimensional surface area of the object are colored by partial extinction of a single wavelength of the light beans of multiple wavelengths from the white light source; and, observing a distribution of at least one of a film thickness and a refractive index along the two-dimensional surface area of the object according to a color distribution of the reflected two-dimensional color image of the two-dimensional surface area of the object.

6. A method as claimed in claim 5, wherein a polarizer is interposed between the white light source and the object to achieve partial extinction of the single wavelength of the light beams of multiple wavelengths from the white light source.

7. A method as claimed in claim 5, wherein a spectroscope is used for quantitative detection of the further reflected light beams of the reflected two-dimensional color image of the two-dimensional surface.

* * * * *